US012778453B2

(12) United States Patent
Gravemaker et al.

(10) Patent No.: US 12,778,453 B2
(45) Date of Patent: Nov. 3, 2026

(54) MONITORING DEVICE, ASSEMBLY OF SAID MONITORING DEVICE WITH A SUPPORT, AND MONITORING SYSTEM

(71) Applicant: Momo Medical Holding B.V., Delft (NL)

(72) Inventors: Menno Laurens Gravemaker, Delft (NL); Thomas Daniël Bakker, Delft (NL); Danny Eldering, Delft (NL)

(73) Assignee: Momo Medical Holding B.V., Delft (NL)

( * ) Notice: Subject to any disclaimer, the term of this patent is extended or adjusted under 35 U.S.C. 154(b) by 310 days.

(21) Appl. No.: 18/577,423

(22) PCT Filed: Jul. 11, 2022

(86) PCT No.: PCT/NL2022/050402
§ 371 (c)(1),
(2) Date: Jan. 8, 2024

(87) PCT Pub. No.: WO2023/282754
PCT Pub. Date: Jan. 12, 2023

(65) Prior Publication Data
US 2024/0324905 A1 Oct. 3, 2024

(30) Foreign Application Priority Data
Jul. 9, 2021 (NL) ...................................... 2028690

(51) Int. Cl.
*A61B 5/11* (2006.01)
*A61B 5/00* (2006.01)

(52) U.S. Cl.
CPC .......... *A61B 5/1115* (2013.01); *A61B 5/0022* (2013.01)

(58) Field of Classification Search
None
See application file for complete search history.

(56) References Cited

U.S. PATENT DOCUMENTS

| | | | | |
|---|---|---|---|---|
| 6,725,401 B1 * | 4/2004 | Lindhorst-Ko | ..... | H04J 14/0227 718/105 |
| 10,898,398 B2 * | 1/2021 | Hayes | .................... | A61G 7/018 |

(Continued)

OTHER PUBLICATIONS

International Search Report and Written Opinion corresponding to PCT/NL2022/050402; Mailed: Sep. 14, 2022, (12 pages).

(Continued)

*Primary Examiner* — Shirley X Jian
(74) *Attorney, Agent, or Firm* — Myers Bigel, P.A.

(57) ABSTRACT

This disclosure presents a monitoring device configured to be associated with a support to monitor a presence of a subject on the support. The monitoring device comprises a sensor configured to collect sensing data on the presence of the subject on the support and a network gateway. The network gateway is configured to receive the sensing data from the sensor and transmit the sensing data to an external network access point and receive auxiliary monitoring data from one or more than one auxiliary sensor external to the monitoring device and transmit the auxiliary monitoring data to the external network access point. Further, an assembly is presented that comprises the monitoring device and a support, wherein the monitoring device is associated with the support. Finally, a monitoring system is presented which comprises the monitoring device and one or more than one auxiliary sensor external to the monitoring device, configured to collect auxiliary monitoring data and transmit the auxiliary monitoring data to the monitoring device.

19 Claims, 3 Drawing Sheets

(56) References Cited

U.S. PATENT DOCUMENTS

| | | | | |
|---|---|---|---|---|
| 2007/0157385 | A1* | 7/2007 | Lemire ................ | A61G 7/0524 5/618 |
| 2013/0245389 | A1 | 9/2013 | Schultz et al. | |
| 2017/0238801 | A1 | 8/2017 | Su et al. | |
| 2018/0185221 | A1 | 7/2018 | Hayes et al. | |
| 2018/0214091 | A1 | 8/2018 | Baker et al. | |
| 2019/0175103 | A1 | 6/2019 | Kogure et al. | |

OTHER PUBLICATIONS

International Preliminary Report on Patentability corresponding to PCT/NL2022/050402; Mailed: Oct. 12, 2023, (23 pages).

* cited by examiner

MONITORING DEVICE, ASSEMBLY OF SAID MONITORING DEVICE WITH A SUPPORT, AND MONITORING SYSTEM

CROSS-REFERENCE TO RELATED APPLICATIONS

This application is a 35 U.S.C. § 371 national phase application of International Application Serial No. PCT/NL2022/050402, filed Jul. 11, 2022, which claims priority to and the benefit of Netherlands Patent Application No. 2028690, filed Jul. 9, 2021, the disclosures of which are hereby incorporated by reference in their entireties.

The present invention relates to monitoring devices that are configured to be associated with a support to monitor presence of a subject on the support. The invention is further related to assemblies of such monitoring devices with such supports as well as to monitoring systems comprising one or more than one monitoring device.

An objective of the present invention is to provide a monitoring device, an assembly and/or a monitoring system that is improved relative to existing technologies, for example with respect to improved connectivity and reliability in communicating data from the monitoring device for distance monitoring, user convenience, safety and compatibility with existing supports, hardware and/or software.

Such objectives as indicated above, and/or other benefits or inventive effects, are attained according to the present disclosure by the combination of features in the appended independent claims. Preferred embodiments are the subject of dependent claims.

The monitoring device may in particular be self-sustained in that it can be arranged in retrofit to existing furniture in a care home or hospital without the need to alter existing infrastructure. For example, existing beds and/or existing network devices can be used and the collection of monitoring devices installed in retrofit extend connectivity via a mesh network formed by the monitoring devices. The monitoring device can thus be implemented readily in existing care settings without requiring hardware alteration of existing infrastructure, including patient supports and network hardware.

In the following description preferred embodiments of the present invention are further elucidated with reference to the drawing, in which.

The following reference signs are used.

Figure 1:
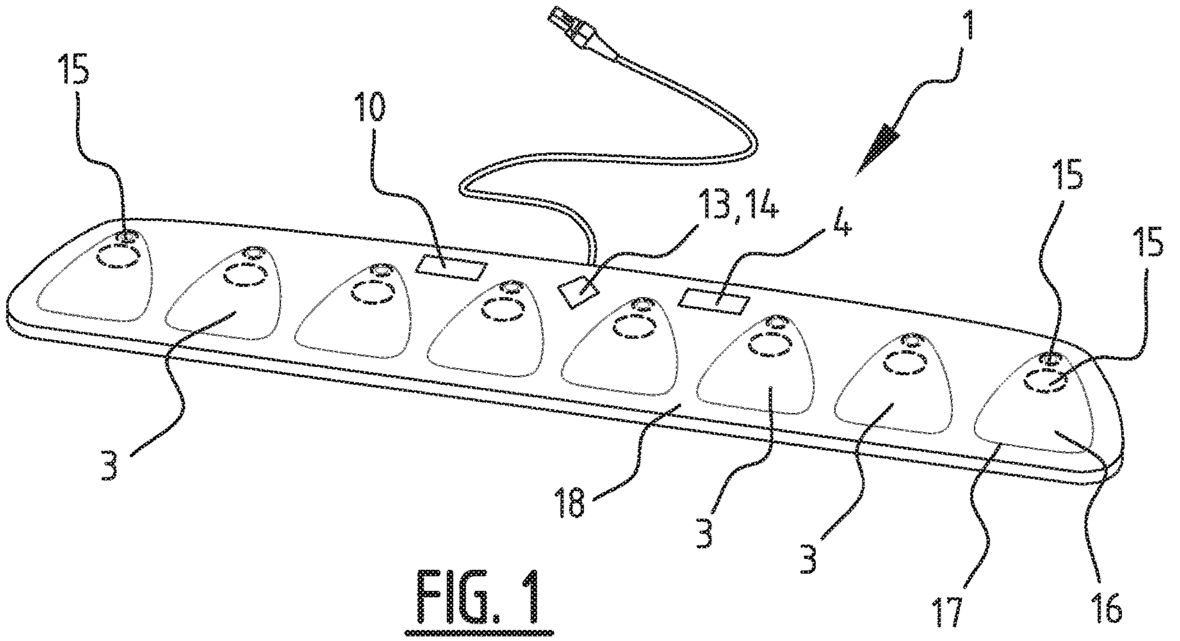
FIG. 1 is a perspective view of a monitoring device according to a preferred embodiment of the present invention.

1 monitoring device
2 support
3 sensor
4 network gateway
5 external network access point
6 auxiliary sensor
7 support surface
8 structural frame
9 mattress or seat
10 motion sensor
11 backup external network access point
12 database
13 radio-frequency identification reader
14 near-field communication reader
15 pressure sensor
16 concentrator
17 pivot
18 base
19 alarm unit
20 localization sensor
21 audio device
22 assembly
23 power source
24 adapter
25 PCB
26 amplification circuit
27 ADC
28 first microchip
29 second microchip
30 third microchip
31 memory
32 output device FIG. 1 shows a monitoring device 1 configured to be associated with a support 2 to monitor a presence of a subject on the support 2. The monitoring device 1 comprises a sensor 3 configured to collect sensing data on the presence of the subject on the support 2 and a network gateway 4. The network gateway 4 is configured to receive the sensing data from the sensor 3 and transmit the sensing data to an external network access point 5 and to receive auxiliary monitoring data from one or more than one auxiliary sensor 6 external to the monitoring device 1 and transmit the auxiliary monitoring data to the external network access point 5.

Figure 2:
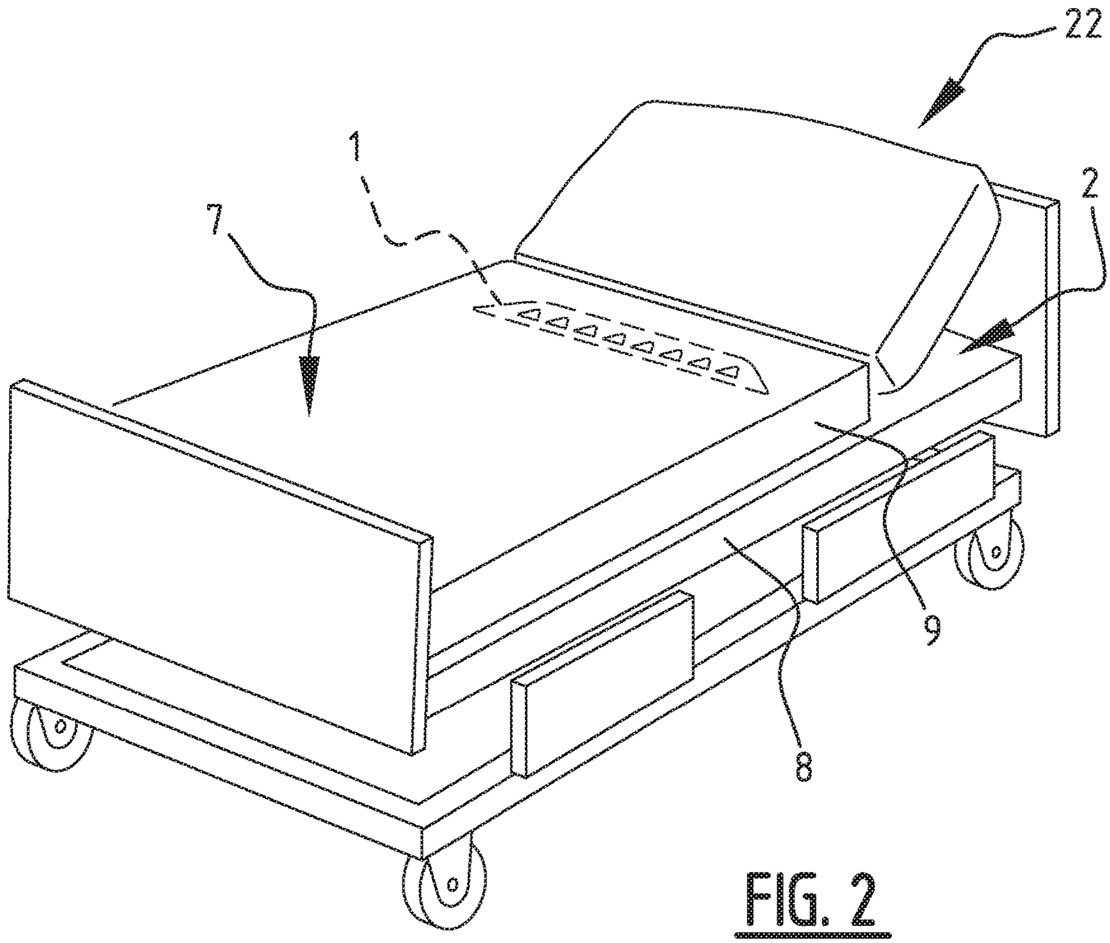
FIG. 2 is a perspective view of an assembly according to a preferred embodiment of the present invention.

Preferably, the monitoring device 1 is further configured to be arranged under a support surface 7 of the support 2 in retrofit, for example under a top surface of a mattress of a bed (e.g. as shown in FIG. 2) or under a seating surface of a piece of furniture, such as a chair, sofa or couch.

Preferably, the monitoring device 1 is a flat elongated object configured to be placed between a structural frame 8 of the support 2 and a mattress or seat 9 of the support 2. Examples of the support 2 include a bed, a hospital bed, a chair, a sofa, a wheelchair, a mobility scooter, a rollator and similar objects.

Preferably, the one or more than one auxiliary sensor 6 comprises the sensor 3 of a further monitoring device 1. The monitoring device 1 and further monitoring device 1 may communicate via their respective network gateways 4 using a meshing communication protocol. Multiple monitoring devices 1 may form a wireless mesh network for efficient communication between the monitoring devices 1 and the external network access point 5 as well as any other auxiliary sensors 6 within reach of the mesh network.

Preferably, the network gateway 4 is further configured to form a node in a mesh network comprising the monitoring device 1 and one or more than one further monitoring device 1 to transmit at least one of the sensing data and the auxiliary monitoring data to the external network access point 5, either directly from the network gateway 4 of the monitoring device 1 or via a further network gateway 4 of the one or more than one further monitoring device 1.

The mesh network may employ routing and/or flooding technology to establish data transmission from one node to another. Though routing technology is preferred for the present invention, the mesh network formed by the monitoring devices 1 may also or alternatively employ flooding technology.

Depending on the topology of the mesh network, a network gateway 4 may take on the role of a root node of the mesh network directly connectable to the external network access point 5 and/or an intermediate node of the mesh network indirectly connectable to the external network access point 5 via further nodes of the mesh network formed by further network gateways 4 of further monitoring devices 1.

The external network access point 5 can be a router, server or similar hardware and may be linked to the internet or a local network of, for example, a care institution where the subject is staying. The external network access point 5 may be linked to or form part of a user terminal, such as a mobile device that can carried by care staff.

The monitoring devices 1 may be configured with server-less capabilities to gather information on current statuses of monitoring devices 1 within the mesh network even in case of failure or the absence of the server or network access point 5. For example, when the server 5 is disabled due to technical disfunction, cyber-attack or internet provider disruption. The monitoring devices 1 in the mesh network can send each other updated information via the mesh network so that at least one or even all of the monitoring devices 1 maintain an overview of the present statuses of each of the monitoring devices 1 connected to the mesh network. A user terminal connected to the mesh network of monitoring devices 1 may gather all sensing data and process it to, for example, determine which relevant data or status changes to output. As soon as connectivity is re-established with the server or external network access point 5, data records on the server 5 can be synchronized from the monitoring devices 1. Live connectivity may not constantly be required.

The monitoring devices 1 within the mesh network can be configured to jointly determine their present status, e.g. regarding the sensing data collected by the sensor and/or auxiliary sensor, while preferably at least one or even each of these monitoring devices 1 records present statuses of all monitoring devices 1 within the mesh network. A separate server 5 is then redundant, avoiding it as a single point of failure in the communication system. An external server 5 may be still of relevance for long-term insights, such as historical data series and synchronization with user terminals outside connectivity range of the monitoring devices 1 or their mesh network. It is also noted that a further monitoring device 1 can be associated with a further support 2, but it can also be associated with the same support 2 as the monitoring device 1.

Mesh networks generally automatically reconfigure when connectivity between its nodes is affected, for example when a node fails or is displaced. When the network gateway 4 is configured to form the node in the mesh network, a communication link is updated or rerouted when the position of the monitoring device 1 within the mesh network is changed, for example when the support 2 to which the monitoring device 1 is associated is moved around.

Preferably, the monitoring device 1 is further configured to detect its displacement within the mesh network and delay reconfiguration of routes within the mesh network until displacement of the monitoring device 1 has ended. Alternatively or additionally, the monitoring device 1 may further be configured to detect displacement of a further monitoring device 1 within the mesh network and delay reconfiguration of routes within the mesh network until displacement of the further monitoring device 1 has ended or connectivity with the further monitoring device 1 is below a predetermined threshold. In this way, automatic updating of the mesh network may be delayed to avoid increased traffic over the mesh network for rerouting operations and thereby reducing network availability for communication of the sending data and/or auxiliary monitoring data which may be of a critical nature.

For example, a moving node of the mesh network can delay updating routes that involve this moving node until the node ceases moving. Such node may detect its own motion by, for example, changes in network connectivity strengths with neighboring nodes and/or a motion sensor 10 coupled to the node (e.g. the network gateway 4 of the monitoring device 1). Conversely, stationary nodes may delay updating routes involving a moving node until such moving node is stationary again and/or such moving nodes is outside connection range or below a predetermined threshold in connectivity strength. Updating routes may not need to be performed for minor displacements not affecting network topology, e.g. when connectivity strength with respect to the displaced node does not go below the predetermined threshold in connectivity strength. Alternatively or additionally, the delay can be a predetermined time period or can depend on a displacement pattern of the node that is being displaced or moved around. When displacement is completed, the updating may commence and then include the now displaced monitoring device at its new position within the mesh network.

Advantages of such delaying of updating routes in a mesh network include prevention of unnecessary data communication over the mesh network by repeated and/or continuous updating operations for moving nodes, which may well occur frequently for monitoring devices 1 arranged with supports 2 that are moveable, such as care beds in a care institution. Further, existing meshing routes can be updated proactively before a node actually moves out of range of nodes through which it was originally routed.

The concept of updating routes in a mesh network is not limited to the application of monitoring devices 1 with a sensor 3 and a network gateway 4, but may be applied more widely independently from the specific implementation presented here.

Displacement of a node can be determined via mesh network connectivity, in particular changes in signal strengths between nodes, and/or via separate motion sensors 10 associated with the node (e.g. the network gateway 4 of the monitoring device 1).

With the above method of updating a mesh network, overloading of the mesh network with continuous updating/rerouting during displacement of one of the monitoring devices 1 is prevented. This is particularly relevant because the monitoring devices 1 are associated with a support 2 that is generally moved more frequently than conventional nodes of a mesh network that are fixed in a building. It may not be necessary to continuously update the mesh network, but only when a repositioning movement has been concluded. For example, moving a subject or patient with the associated support (e.g. bed or wheelchair) is generally performed under supervision of care personnel, so there may be no need to tax the mesh network with constant rerouting while subject and/or support are being moved around a care institution but only when the destination is reached and direct supervision by care personnel (again) ceases. Also when the monitoring device 1 is reused for a different support/subject at a different location within the mesh network, continuous updating during displacement is often not desired.

As an alternative or in addition to the above, it is suggested that the monitoring device 1 does not accept connections from other monitoring devices 1 in the mesh network when it is moved/displaced while is continuous to make connections to other monitoring devices 1, e.g. act as a so-called leaf node within the mesh network.

Preferably, the network gateway 4 is further configured to select a first communication protocol to transmit at least one of the sensing data and the auxiliary monitoring data to the external network access point 5 and/or to select the first communication protocol or a second communication protocol to receive auxiliary monitoring data from a further monitoring device 1 comprised by the one or more than one auxiliary sensor 6 and/or to select the first communication protocol, the second communication protocol or a third communication protocol to receive auxiliary monitoring data from at least one auxiliary sensor 6 from among the one or more than one auxiliary sensor 6 not being a further monitoring device.

The first communication protocol may be used to communicate directly between the monitoring device 1 and the external network access point 5 (irrespective of whether the mesh network of multiple monitoring devices 1 is available or used), while the first and/or second communication protocol is used within the mesh network. When the first and second communication protocols are the same, the external network access point 5 can be regarded as another or final node in the mesh network. The first, second and/or third communication protocol may be used to communicate with external auxiliary sensors 6 that are not monitoring devices 1, such as other healthcare sensors peripheral to the monitoring device 1.

Preferably, the first communication protocol is used to transmit the sensing data and the auxiliary monitoring data to the external network access point, the second communication protocol is used to receive auxiliary monitoring data from a further monitoring device comprised by the one or more than one auxiliary sensor and/or the third communication protocol is used to receive auxiliary monitoring data from at least one auxiliary sensor from among the one or more than one auxiliary sensor not being a further monitoring device.

Preferably, the first communication protocol is selected from a group comprising an IEEE 802.3 based protocol, an IEEE 802.11 based protocol, WLAN, Wi-Fi, 2.4 GHz band Wi-Fi, 5 GHz band Wi-Fi, 4G and 5G.

Preferably, the second communication protocol is selected from a group comprising an IEEE 802.15.4 based protocol, a meshing protocol, WLAN, Wi-Fi, 2.4 GHz band Wi-Fi, 5 GHz band Wi-Fi, 868 MHz band wireless meshing, 915 MHz wireless meshing and 434 MHz wireless meshing.

Preferably, the third communication protocol is selected from a group comprising an IEEE 802.15.4 based protocol, WLAN, Wi-Fi, 2.4 GHz band Wi-Fi, 5 GHz band Wi-Fi, Bluetooth®, BLE, Zigbee®, LoRa®, RFID and NFC. The third communication protocol can also be used by the monitoring device 1 to communicate with the user terminal instead of, or in addition to, communicating with the external network access point 5 via the first communication protocol. The monitoring device 1 may alternatively or additionally communicate with the user terminal via any of the first communication protocol and the second communication protocol, or indeed via a fourth communication protocol which may be separately selected from the communication protocols listed above for the first, second and third communication protocols. The user terminal, preferably in the form of a mobile device, can be configured to receive sensing data directly from the monitoring device 1 as well as auxiliary sensing data, preferably including sensing data from further monitoring devices 1 forming a mesh network, while omitting a server or external network access point 5 in between. This provided a distributed solution for e.g. care home staff to monitor patients in their care. The user terminal can be configured to access the external network access point 5, or even itself form the external network access point 5 for the monitoring device 1.

Figure 3:
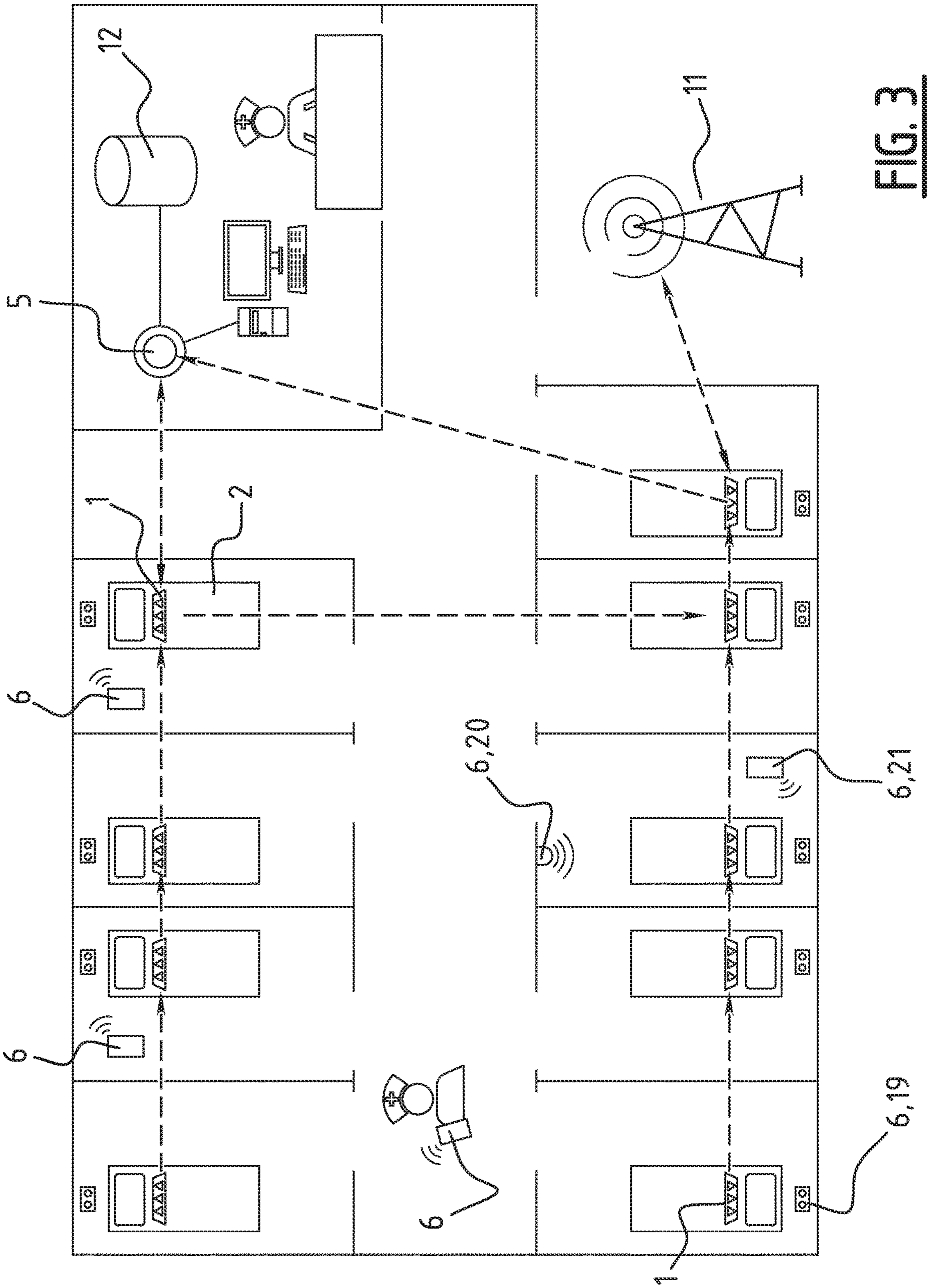
FIG. 3 is a schematic illustration of a system according to a preferred embodiment of the present invention.

Preferably, the network gateway 4 is further configured to establish communication with a backup external network access point 11 when connectivity to the external network access point 5 falls below a reliability threshold. The reliability threshold may be based on connectivity strength, frequency of interruptions, available bandwidth, at similar measures. For example, the network gateway 4 may further be configured to communicate with the external network access point 5 via a wireless local area network protocol, such as Wi-Fi or an IEEE 802.11 based communication protocol, and communicate with the backup external network access point 11 via a telecommunication communication protocol such as 4G or 5G. FIG. 3 presents a schematic illustration of this case.

The first, second and third communication protocols may be prioritized for communication by the monitoring device 1 in this order. For example, the first or primary communication protocol may involve wireless local area networking or Wi-Fi, the second or secondary communication protocol may involve mesh networking and the third or tertiary communication protocol may involve 868 MHz bandwidth and/or a telecommunication protocol. The secondary and tertiary communication protocols may form a back-up for respectively the primary and both the primary and secondary communication protocols.

It is preferred to select the first, second and third communication protocols in at least two different frequency bandwidths. In case one of these frequency bandwidths does not provide sufficient reliability, e.g. due to blocking, interference or crowding, another one can be used.

Using multiple frequency bands can have a further advantage in improving localization of the monitoring device 1. With a single frequency band, relative displacement of the monitoring device 1 can be determined, i.e. relative to other presumably stationary devices communicating to the monitoring device 1 via said frequency band. Use of multiple frequency bands aids in distinguishing between relative and absolute displacement of the monitoring device 1, i.e. whether it is in fact being displaced or that device connected to it are being moved. Multiple transceivers may be used to implement multiple frequency bands, preferably at least three, e.g. one for each communication protocol.

Reliability in connectivity can be increased by using multiple communication protocols in parallel and/or as back-up of each other. For example, if something is blocking or disturbing the 2.4 GHz band, Wi-Fi as well as mesh Wi-Fi networking can be affected. This can obscure determining whether a monitoring device 1 is suffering from connectivity issues or is simply switched off. Using a back-up communication protocol, e.g. 868 MHz or any of the unaffected first, second or third communication protocols, to attempt communication with a monitoring device 1 can then resolve the issue and provide knowledge on whether it is indeed switched off or that communication via e.g. the primary and/or secondary communication protocols is indeed disturbed. This information can be shared through e.g. the mesh network to update all connected monitoring devices 1 on its status.

Preferably, the network gateway 4 is further configured to transmit identification data associated with at least one of the support 2 and the subject along with the sensing data. In this way, the sensing data can be coupled to a particular support 2 and/or subject and may be stored appropriately in a database 12, which may be located in an Ethernet, internet or cloud-base service.

Preferably, the network gateway 4 is further configured to transmit auxiliary identification data associated with at least one of the auxiliary sensor 6 and the subject along with the auxiliary monitoring data. In this way, the auxiliary monitoring data can be coupled to a particular auxiliary sensor 6 (e.g. a further monitoring device 1) and/or subject and may be stored appropriately in an database or cloud 12.

Preferably, the network gateway 4 is further configured to transmit routing data associated with a communication route selected for transmission to the external network access point 5 along with at least one of the sensing data and the auxiliary monitoring data. The communication route may be predetermined, for example by routing operations of a mesh network formed by network gateways 4 of a plurality of monitoring devices 1.

Preferably, the monitoring device 1 further comprises a motion sensor 10 configured to collect displacement data of the monitoring device 1. The motion sensor 10 may be an accelerometer, a gyroscope, a GPS device, a localization module using local network connectivity strength such as connectivity strengths within the mesh network, and other devices known to the person skilled in the art.

The sensor 3 of the monitoring device 1 may comprise at least one of a radio-frequency identification reader 13 and a near-field communication reader 14, for example for detection of a radio-frequency identification tag or a near-field communication tag carried by the subject. Alternatively or additionally, the sensor 3 of the monitoring device 1 may comprise one or more than one pressure sensor 15, for example a force-sensing resistor and/or a piezoelectric element.

Further, the sensor 3 may comprises an array of pressure sensors 15. An array of pressure sensors 15 can be used to discriminate between postures of the subject when present on the support 2.

Preferably, at least one pressure sensor 15 is coupled to a concentrator 16 configured to concentrate pressure exerted by the subject on the support 2 and transfer the concentrated pressure to the pressure sensor 15. As illustrated in FIG. 1, the concentrator 16 comprises a pivot 17 that is configured to pivotably arrange the concentrator 16 relative to a base 18 of the monitoring device 1. The pivot is arranged at a first side of the concentrator 16 and the concentrator 16 is configured to contact the pressure sensor 15 at a lever distance from the pivot 17.

The one or more than one auxiliary sensor 6 may comprises at least one of the following: an alarm unit 19 configured for activation by the subject, an incontinence sensor configured to be worn by the subject, an localization sensor 20 configured to localize the subject when not present on the support, and an audio device 21 configured for speech communication between the subject and a healthcare provider.

The alarm unit 19 can worn by the subject as a necklace, bracelet, smart watch or the like. Further, the alarm unit 19 can be positioned near the support 2 or be arranged as a wall-mounted button or drawstring.

The localization sensor 20 can be implemented in various ways. For example, it can be coupled to a door of a room in which the support 2 is positioned to detect opening of this door indicating that the subject normally associated with the support 2 likely leaves said room. Further, the localization sensor 20 can be embodied as a motion sensor registering whether motion is detected in a field of view.

The invention may thereby not only improve connectivity for the sensor 3 of the monitoring device 1, but also for any auxiliary sensors 6 in its neighborhood, such as further sensors peripheral to the monitoring device 1.

FIG. 2 shows an assembly 22 comprising a monitoring device 1 and a support 2, wherein the monitoring device 1 is associated with the support 2. In the illustrated example, the support is a bed 2 and the monitoring device 1 is positioned on the structural frame 8 of the bed 2 and below the mattress 9 of the bed 2.

In general, the monitoring device 1 may be arranged under a support surface 7 of the support 2 and/or embedded in the support 2 to form the assembly 22.

Further, the support 2 may comprise a structural frame 8 and a mattress or seat 9. It is then preferred that the monitoring device 1 is a flat elongated object placed between the structural frame 8 and the mattress or seat 9. The support may be a piece of furniture selected from a group comprising a bed such as a normal bed, a care or hospital bed or a smart bed, a chair, a sofa, a couch or any of the objects mentioned above.

Preferably, the support 2 is connectable to an external power source 23 to power the monitoring device 1. Such power source 23 may be wired, such as a mains supply, or may be wireless, such as an induction charging plate for a battery of the support 2. Further, the support 2 may also comprise a battery chargeable via the external power source 23 and configured to power the monitoring device 1. Power can be provided to the monitoring device 1 even when not connected to the external power source 23, for example when moving the support 2 whereby a mains connection can temporarily not be maintained. Risk of power interruption and thus interruption of data communication can be reduced.

FIG. 3 shows a monitoring system comprising a monitoring device 1 and one or more than one auxiliary sensor 6 external to the monitoring device 1. The auxiliary sensor 6 is configured to collect auxiliary monitoring data and transmit the auxiliary monitoring data to the monitoring device 1. Direct communication via e.g. WLAN or Wi-Fi is possible in the system, though it is preferred that a mesh network is formed.

Preferably, the one or more than one auxiliary sensor comprises the sensor 3 of a further monitoring device 1.

Preferably, the network gateways 4 of the monitoring device 1 and the further monitoring device 1 each form a node of a mesh network to transmit at least one of the sensing data and the auxiliary monitoring data to the external network access point 5. Alternatively, the backup external network access point 11 may be used.

The mesh network improves reliability of connectivity even for remote monitoring devices 1 and/or auxiliary sensors 6 that would otherwise be too far away from a network access point 5. In FIG. 3, this is illustrated along an example of a care institution in which various rooms are served by a single external network access point 5. Also for distant rooms, critical data must be communicated reliably and fast to care personnel, for example to a control room of a night-shift nurse.

The monitoring device 1 and/or the further monitoring device 1 of the monitoring system may be comprised in an assembly 22. In FIG. 3, a plurality of assemblies 22 is each formed by a bed 2 and associated monitoring device 1.

Figure 4:
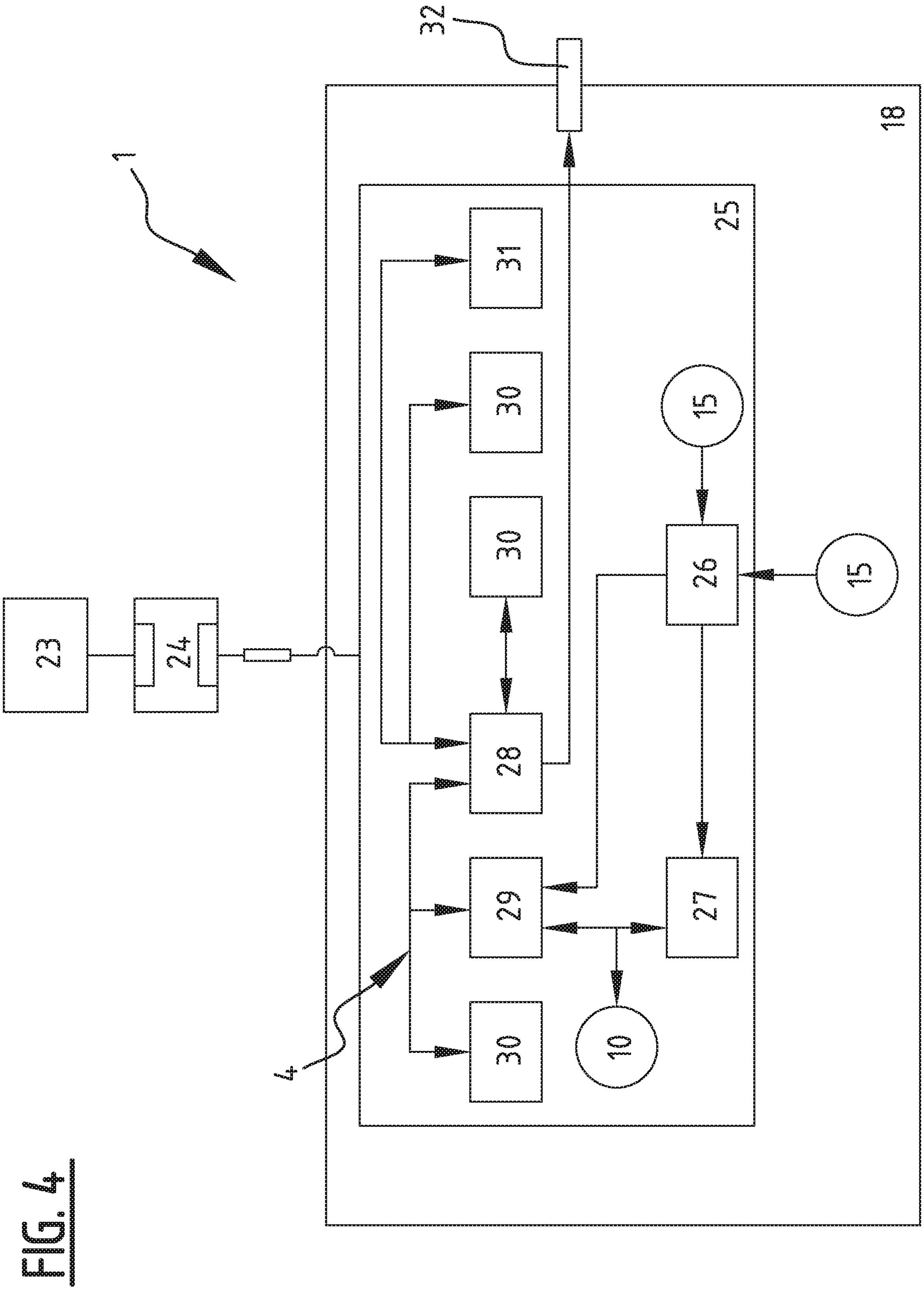
FIG. 4 is a schematic illustration of hardware components of a monitoring device according to a preferred embodiment of the present invention.

FIG. 4 shows a schematic layout of various hardware components in a preferred embodiment of the monitoring device 1. The monitoring device 1 is powered via a power source 23, which may be a battery of the support 2, and may include an AC/DC adapter 24. A PCB 25 carries various electronic components and ensures appropriate electrical connections.

Pressure sensors 15 provide signals to an amplification circuit 26 and on to an ADC 27 and/or one or more than one microchip 28, 29, 30. The network gateway 4 can comprise one or more than one microchip 28, 29, 30 to implement the first, second and/or third communication protocol. In FIG. 4, multiple third microchips 30 are illustrated, which may each provide connectivity using another or the same communication protocol, e.g. 868 MHz connection, Bluetooth® and Wi-Fi. Similarly, multiple first microchips 28 and/or second microchips 29 can be employed.

Preferably, the network gateway 4 comprises a first microchip 28 configured to execute at least the first communication protocol and/or a second microchip 29 configured to execute at least the second communication protocol and/or a third microchip 30 configured to execute at least the third communication protocol. When a separate microchip 28, 29, 30 is employed for each communication protocol, parallel execution of communication protocols is possible to provide faster and more reliable data communication, in particular from the sensor 3 and/or the auxiliary sensor 6 to the external network access point 5.

Preferably, each of the first, second and third microchips 28, 29, 30 is configured to execute each of the first, second and third communication protocols, or at least two of these, for example the first and second communication protocols. Different communication lines or networks can be operated using the same communication protocol, such as Wi-Fi, for example by employing multiple microchips communicating in parallel each with a different network identifier, e.g. SSID. Microchips 28, 29, 30 suitable for this purpose are sold under the name ESP32, though other suitable microchips are generally available.

A memory 31 may be provided to store instructions for the microchips 28, 29, 30, one of which may also include a processor for the monitoring device 1. Though the memory 31 may also be configured to store data obtained by the sensor 3 and/or auxiliary sensor(s) 6, it is preferred that such data is directed transmitted via the network gateway 4 to e.g. the database 12 as soon as possible without permanent storage in the monitoring device 1 itself.

Further, an output device 32 can be provided for audio and/or visual output to users of the monitoring device 1.

Although preferred embodiments of the invention are described and shown, these are intended only to illustrate the invention and not to limit in any way the scope of the invention. Accordingly, it should be understood that where features mentioned in the appended claims are followed by reference signs, such signs are included solely for the purpose of enhancing the intelligibility of the claims and are in no way limiting on the scope of the claims. Furthermore, it is particularly noted that the skilled person can combine technical measures of the different embodiments. The scope of protection is defined solely by the following claims.

The invention claimed is:

1. Monitoring device configured to be associated with a support to monitor a presence of a subject on the support, the monitoring device comprising:

a sensor configured to collect sensing data on the presence of the subject on the support; and a network gateway configured to:

receive the sensing data from the sensor and transmit the sensing data to an external network access point;

receive auxiliary monitoring data from one or more than one auxiliary sensor external to the monitoring device and transmit the auxiliary monitoring data to the external network access point;

wherein the network gateway is further configured to form a node in a mesh network comprising the monitoring device and one or more than one further monitoring device to transmit at least one of the sensing data and the auxiliary monitoring data to the external network access point, either directly from the network gateway of the monitoring device or via a further network gateway of the one or more than one further monitoring device; and wherein the network gateway is further configured to transmit auxiliary identification data associated with at least one of the auxiliary sensor and the subject along with the auxiliary monitoring data;

wherein the monitoring device is configured with serverless capabilities to gather information on current statuses of monitoring devices within the mesh network, and wherein the monitoring device is configured to send other monitoring devices in the mesh network updated information for at least one or all of the monitoring devices to maintain an overview of the present statuses of each of the monitoring devices connected to the mesh network when transmitting at least one of the sensing data and the auxiliary monitoring data to the external network access point is interrupted.

2. Monitoring device of claim 1, wherein the monitoring device is further configured to be arranged under a support surface of the support in retrofit.

3. Monitoring device of claim 1, wherein the monitoring device is a flat elongated object configured to be placed between a structural frame of the support and a mattress or seat of the support.

4. Monitoring device of claim 1, wherein the one or more than one auxiliary sensor comprises a sensor of a further monitoring device.

5. Monitoring device of claim 3, wherein at least one of:

the monitoring device is further configured to detect its displacement within the mesh network and delay reconfiguration of routes within the mesh network until displacement of the monitoring device has ended; and the monitoring device is further configured to detect displacement of a further monitoring device within the mesh network and delay reconfiguration of routes within the mesh network until displacement of the further monitoring device has ended or connectivity with the further monitoring device is below a predetermined threshold.

6. Monitoring device of claim 1, wherein the network gateway is further configured to select at least one of:

a first communication protocol to transmit at least one of the sensing data and the auxiliary monitoring data to the external network access point;

the first communication protocol or a second communication protocol to receive auxiliary monitoring data from a further monitoring device comprised by the one or more than one auxiliary sensor; and the first communication protocol, the second communication protocol or a third communication protocol to receive auxiliary monitoring data from at least one auxiliary sensor from among the one or more than one auxiliary sensor not being a further monitoring device and/or to communicate with a user terminal.

7. Monitoring device of claim 6, wherein the network gateway comprises at least one of:

a first microchip configured to execute at least the first communication protocol;

a second microchip configured to execute at least the second communication protocol; and a third microchip configured to execute at least the third communication protocol.

8. Monitoring device of claim 1, wherein the network gateway is further configured to establish communication with a backup external network access point when connectivity to the external network access point falls below a reliability threshold.

9. Monitoring device of claim 8, wherein the network gateway is further configured to:

communicate with the external network access point via an IEEE 802.11 based communication protocol; and communicate with the backup external network access point via a telecommunication communication protocol.

10. Monitoring device of claim 1, wherein the network gateway is further configured to transmit identification data associated with at least one of the support and the subject along with the sensing data.

11. Monitoring device of claim 1, wherein the network gateway is further configured to transmit routing data associated with a communication route selected for transmission to the external network access point along with at least one of the sensing data and the auxiliary monitoring data.

12. Monitoring device of claim 1, further comprising a motion sensor configured to collect displacement data of the monitoring device.

13. Monitoring device of claim 1, wherein the sensor comprises at least one of:

a radio-frequency identification reader;

a near-field communication reader; and a pressure sensor.

14. Monitoring device of claim 1, wherein the one or more than one auxiliary sensor comprises at least one of:

an alarm unit configured for activation by the subject;

an incontinence sensor configured to be worn by the subject;

an localization sensor configured to localize the subject when not present on the support; and an audio device configured for speech communication between the subject and a healthcare provider.

15. Assembly comprising:

a monitoring device according to claim 1; and a support, wherein the monitoring device is associated with the support.

16. Assembly of claim 15, wherein the monitoring device is at least one of:

arranged under a support surface of the support; and embedded in the support.

17. Assembly of claim 15, wherein:

the support comprises a structural frame and a mattress or seat; and the monitoring device is a flat elongated object placed between the structural frame and the mattress or seat.

18. Assembly of claim 15, wherein the support is connectable to an external power source to power the monitoring device.

19. Assembly of claim 18, wherein the support further comprises a battery chargeable via the external power source and configured to power the monitoring device.

* * * * *